United States Patent
Kaplan et al.

(10) Patent No.: US 12,232,942 B1
(45) Date of Patent: Feb. 25, 2025

(54) INCONTINENCE IMPLANT MEDICAL DEVICE

(71) Applicants: Eugene Kaplan, Lompoc, CA (US); Oleg Mazur, Nauheim (DE)

(72) Inventors: Eugene Kaplan, Lompoc, CA (US); Oleg Mazur, Nauheim (DE)

( * ) Notice: Subject to any disclaimer, the term of this patent is extended or adjusted under 35 U.S.C. 154(b) by 0 days.

(21) Appl. No.: 18/751,586

(22) Filed: Jun. 24, 2024

(51) Int. Cl.
 *A61F 2/00* (2006.01)

(52) U.S. Cl.
 CPC .... *A61F 2/0022* (2013.01); *A61F 2220/0041* (2013.01)

(58) Field of Classification Search
 CPC ............... A61F 2/0022; A61F 2220/0041
 See application file for complete search history.

(56) References Cited

U.S. PATENT DOCUMENTS

| | | | |
|---|---|---|---|
| 2008/0021263 | A1 | 1/2008 | Escude et al. |
| 2010/0261950 | A1* | 10/2010 | Lund ............... A61F 2/0045 600/30 |
| 2014/0235932 | A1* | 8/2014 | Ogdahl ............ A61F 2/0045 600/30 |

FOREIGN PATENT DOCUMENTS

WO 2019058180 A2 3/2019

OTHER PUBLICATIONS

Surgical treatment of urinary stress incontinence using a method for postoperative adjustment of sling tension (Remeex System)by Xavier Iglesias, Int Urogynecol Journal (2003) 14: 326-330 DOI 10.1007/s00192-003-1072-1, Published Sep. 6, 2003 by International Urogynecological Association.
Does 'Tension-Free' Solve All Stress Incontinence? Our Experience of Using a Re-Adjustable Sling (Remeex) In 58 Complicated Cases by Errando C, Prados M, Araño P, Villavicencio H, Fundacion Puigvert.
Advantages of suburethral readjustable slings for the treatment of stress urinary incontinence in women by E. Kaplan at Center for Advanced Gynecologic Surgery, Walnut Creek, USA, for 2009 International Urogynecological Association.

* cited by examiner

*Primary Examiner* — Carrie R Dorna
*Assistant Examiner* — Joshua Daryl D Lannu
(74) *Attorney, Agent, or Firm* — Plager Schack LLP; Mark H. Plager, Esq.; Naomi Mann, Esq.

(57) ABSTRACT

A system for treating urinary incontinence provides an implant device that holds threads of a sling/graft, and further allows for adjustment of the threads. The implant device includes a bobbin on which the threads may be wound, a drive assembly configured to rotate the bobbin, the drive assembly comprising a shaft and a gear assembly, the gear assembly configured to transfer a rotational motion of the shaft to the bobbin to effectuate an axial rotation of the bobbin. The bobbin and drive assembly may be retained in a device housing. The drive assembly may be cycloidal for a high gear ratio with reduced device size.

18 Claims, 4 Drawing Sheets

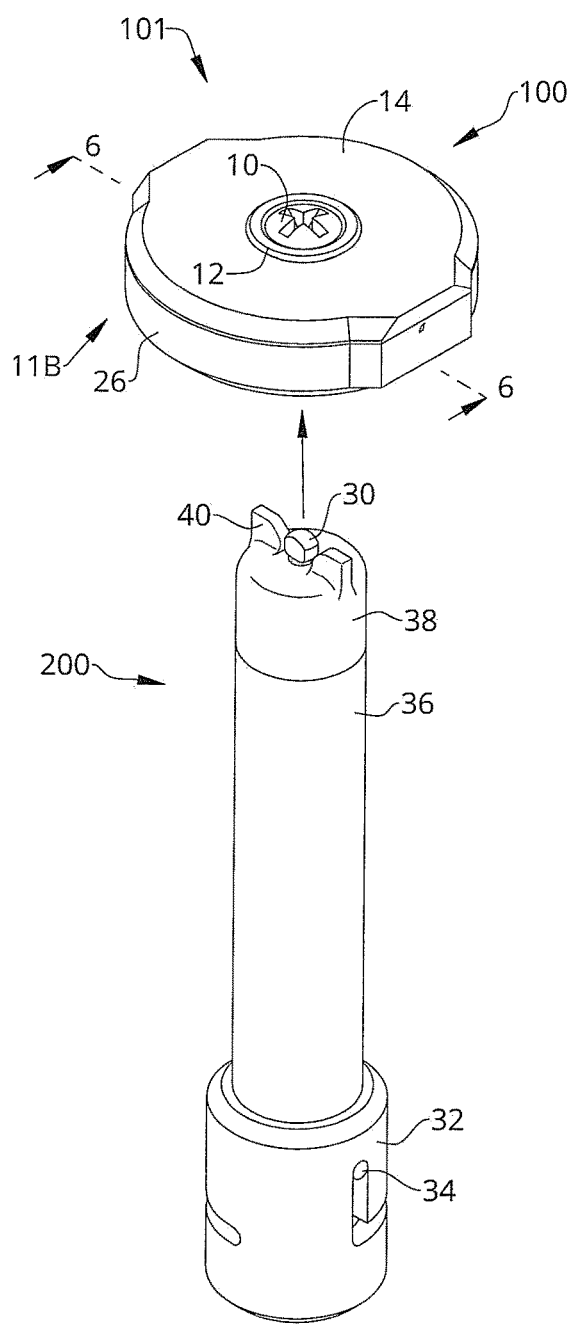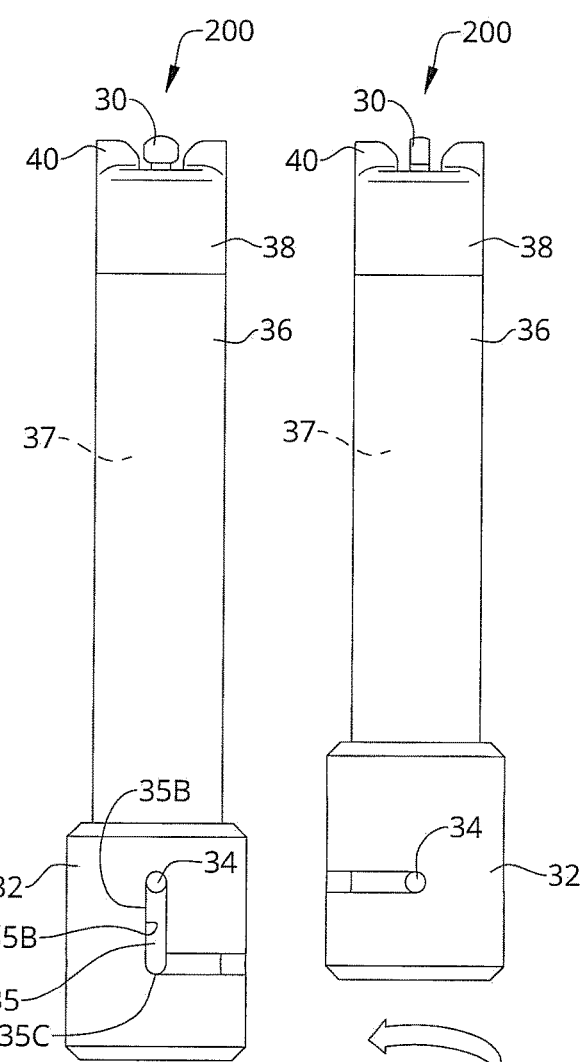
FIG.1
FIG.2
FIG.3

INCONTINENCE IMPLANT MEDICAL DEVICE

BACKGROUND

The present disclosure relates generally to incontinence implant devices and systems.

Urinary incontinence may be treated via an implant device in both men and women. As such, improved incontinence implant devices and systems which minimize invasiveness and patient's discomfort are desirable.

SUMMARY

According to various embodiments, disclosed is an incontinence implant medical system which provides an implant device with bobbin system which holds the threads of a sling/graft under tension, while allowing for convenient tension adjustment with further re-adjustment any time after the device has been implanted. In embodiments, the mechanical components of the device, including eccentric motion gear drive, provide a compact device with reduced size/thickness, with greater wearing comfort and minimized surgical operation time.

In certain embodiments, the implant device may comprise a bobbin on which the threads of an implanted sling may be wound; a drive assembly configured to rotate the bobbin, the drive assembly comprising a shaft and a gear assembly, the gear assembly configured to transfer a rotational motion of the shaft to the bobbin to effectuate an axial rotation of the bobbin, wherein the bobbin and drive assembly are retained in a device housing, configured to allow threads wound on the bobbin to pass, and wherein the implant device is configured to allow for adjustment of a length of threads wound on the bobbin via rotation of the bobbin. In some embodiments, the bobbin, shaft, and gear assembly are aligned about a rotational axis which may be a parallel and/or co-axial. In certain embodiments, the drive assembly is a cycloidal drive. In some embodiments, the gear assembly comprises an internal gear coupled to the shaft, the shaft configured to rotate about said parallel and/or coaxial rotational axis and to drive a cycloidal rotation of the internal gear. In some further embodiments, the shaft comprises a symmetrical bottom portion and an eccentric shaft neck. In certain embodiments, the eccentric shaft neck is directly coupled to the internal gear. In some embodiments, the device further comprises a gear ring, wherein external teeth of the internal gear are configured to cycloidally roll against internal teeth in the gear ring when the internal gear is driven by the shaft. In some further embodiments, the gear ring is an integral component of the device housing. In certain embodiments, the gear assembly further comprises an eccentricity compensator between the bobbin and the internal gear, the eccentricity compensator being coupled to an underside of the bobbin and to an upper side of the internal gear and is configured to drive a cylindrical rotation of the bobbin. In some embodiments, the eccentricity compensator includes a first pair of opposing guide slots configured to slidable engage a corresponding pair of upper tabs in the cycloid gear, and a second pair of opposing guide slots configured to slidably engage a corresponding pair of bottom tabs in the underside of the bobbin, wherein as the internal gear cycloidally rotates, the upper tabs slide within the first pair of guide slots and the bottom tabs slide within the second pair of guide slots.

In certain embodiments, the drive assembly may be actuated via a tool configured to detachably engage the shaft for driving a rotation of the shaft. In some embodiments, the shaft includes a bottom portion which provides an inlet hole for receiving said tool, the device housing including a bottom opening that provides access to said inlet hole in the shaft. In some further embodiments, the device housing comprises a top cover and a bottom cover configured to interlock with the top cover. In certain embodiments, the device housing includes opposing holes through which threads wound on the bobbin may pass. In some embodiments, an upper section of the bobbin comprises a central threaded hole configured to receive a screw for affixing threads wound on the bobbin. In further embodiments, the upper section of the bobbin includes openings through which the ends of threads wound on the bobbin may pass, wherein the upper section of the bobbin is shaped to enable said screw to capture the ends of said threads when said threads are wound on the bobbin and when the screw is threaded through said central threaded hole, wherein the ends of the threads are captures between a head of the screw and a wall surrounding the central threaded hole. In certain embodiments, the wall surrounding the central threaded hole is a well which is shaped to match the shape of the screw head. In some embodiments, the well has a conical, parabolic, and/or concaved profile. In some embodiments, a top section of the housing includes an opening configured to allow said screw to pass into the threaded hole in the upper section of the bobbin. In some further embodiments, the device is disc shaped with a low axial length to diameter ratio.

BRIEF DESCRIPTION OF THE FIGURES

The detailed description of some embodiments of the invention will be made below with reference to the accompanying figures, wherein the figures disclose one or more embodiments of the present invention.

FIG. 1 is perspective view of components of an incontinence treatment system including an implant device and tension adjustment tool, according to certain embodiments.

FIG. 2 is a side view of the tension adjustment tool in an unlocked position.

FIG. 3 is a side view of the tension adjustment tool in a locked position, showing motion of the tool handle.

DETAILED DESCRIPTION OF CERTAIN EMBODIMENTS

Figure 4A:
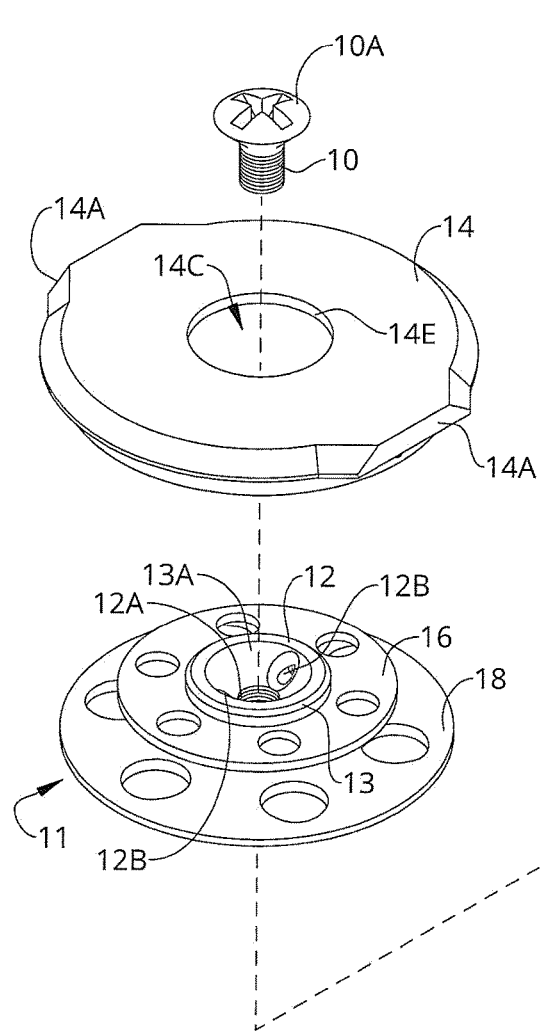
FIG. 4A is an exploded view of the implant device.
Figure 4A:
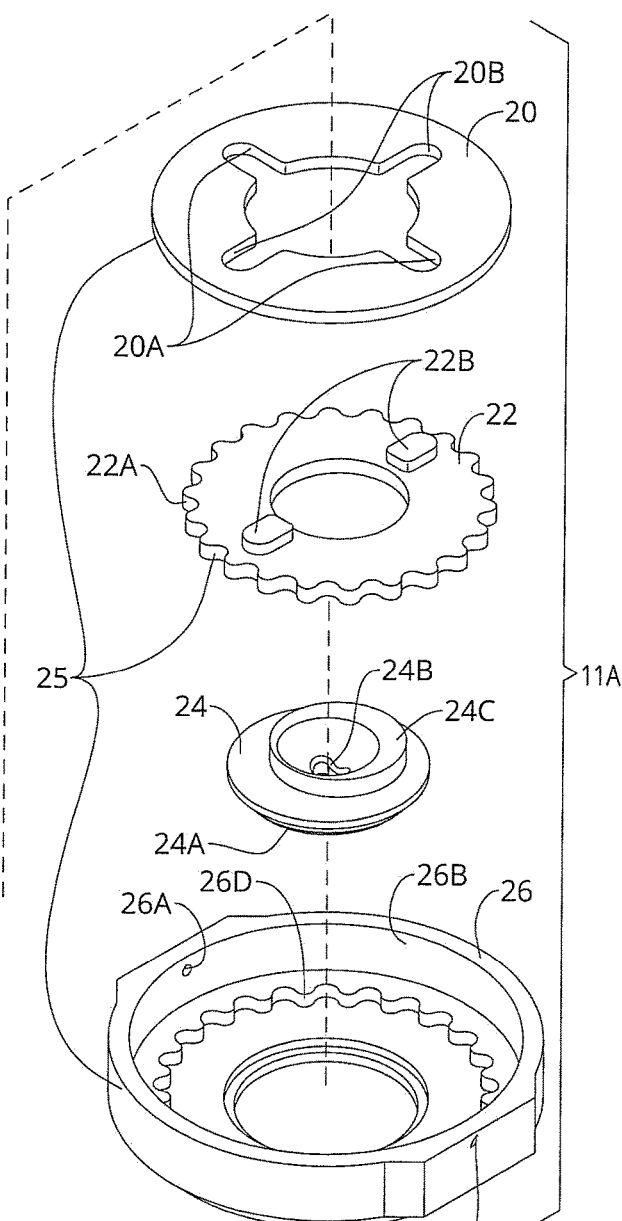
Figure 4B:
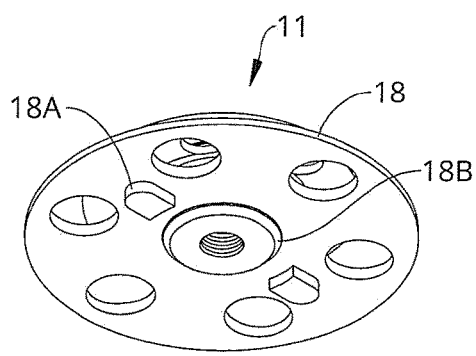
FIG. 4B is a bottom perspective view of a bobbin component of the implant device.
Figure 4C:
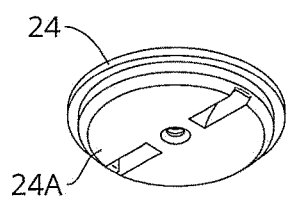
FIG. 4C is a bottom perspective view of a shaft component of the implant device.
Figure 5:
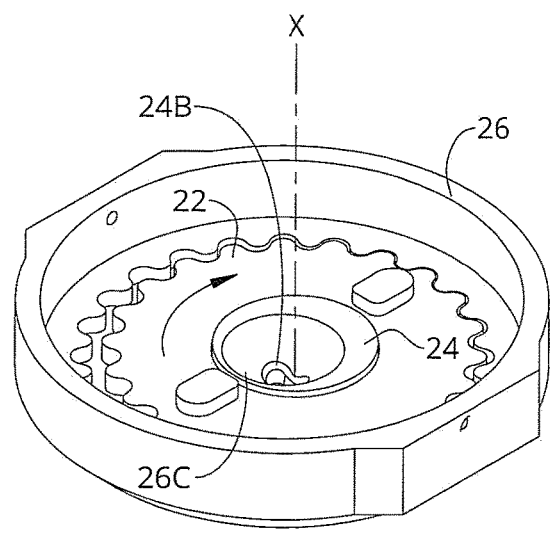
FIG. 5 is a perspective view of a lower portion of the implant device according to certain embodiments, depicting cycloidal gearing.
Figure 6:
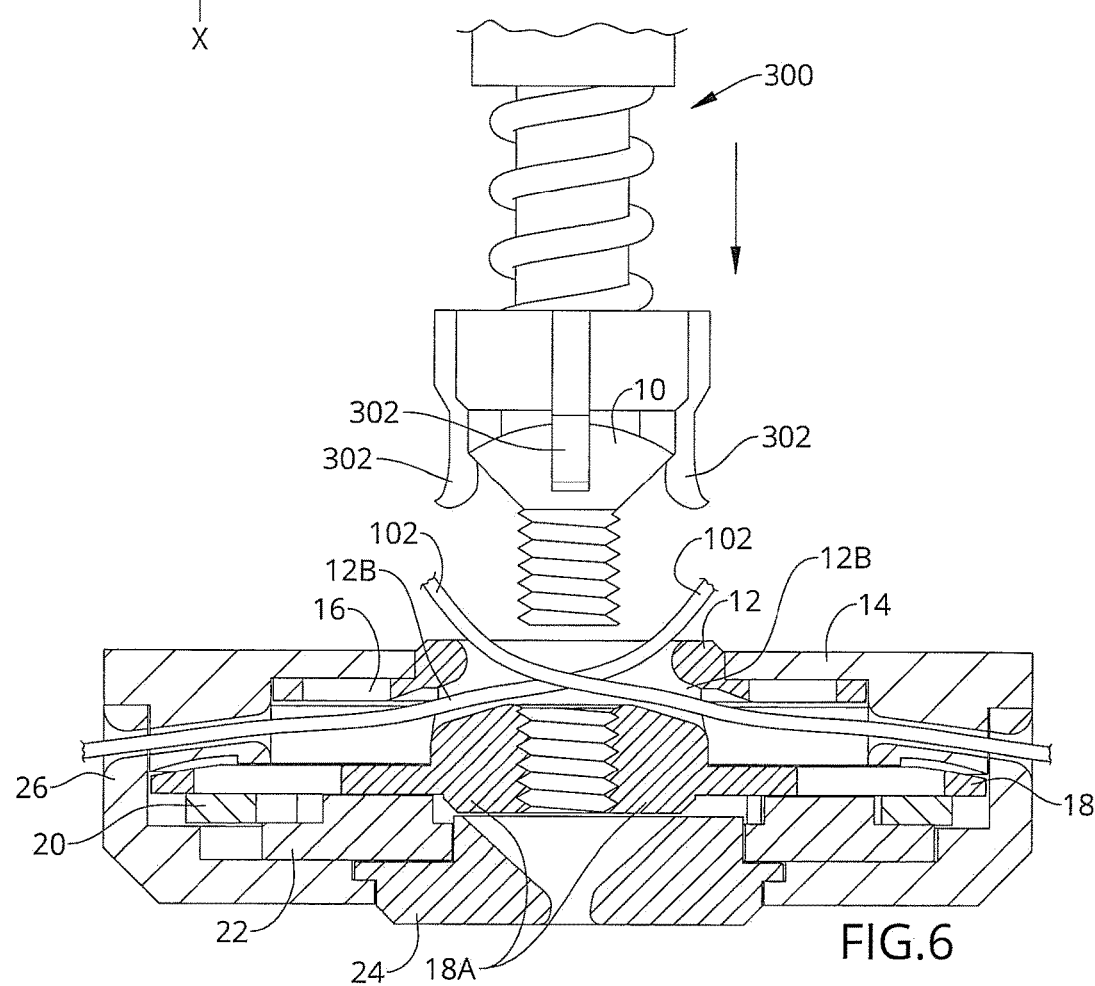
FIG. 6 is a partial sectional view taken along line 6-6 in FIG. 1, illustrating use of a screw installation tool for affixing threads within the implant device via a screw locking mechanism according to certain embodiments.
Figure 7:
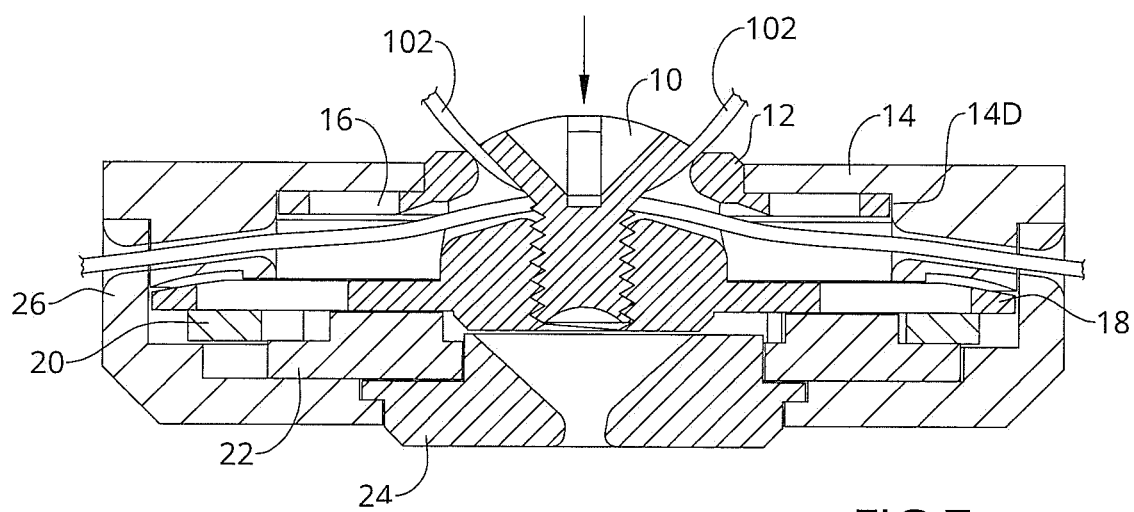
FIG. 7 is a section view of the implant device taken along line 6-6 in FIG. 1, depicting the screw installed.

According to various embodiments, as depicted in FIGS. 1-7, disclosed is an incontinence implant medical system 101 comprising an implant device 100 for treating stress urinary incontinence in male or female patients. Implant device 100 serves to hold and adjust threads 102 of a sling/graft (not shown), and allows for subsequent re-adjustment in the length of the threads after device 100 has been implanted. As such, the tension of the sling may be readjusted if necessary, at any time after implantation. In certain embodiments, implant device 100 has a flat, low profile structure in anatomically friendly form which may remain in the body indefinitely.

In certain embodiments, implant device 100 includes a spool system for winding threads 102, comprising a bobbin 11 on which threads 102 are wound, and a drive assembly 11A configured to rotate bobbin 11 for adjusting the tension in threads 102. In further embodiments, bobbin 11 and drive assembly 11A are retained in a device housing 11B through which threads 102 may pass. In some embodiments, drive assembly 11A may be actuated via a detachable tension tool 200. In certain embodiments, drive assembly 11A may be a cycloidal drive. In further embodiments, implant device 100 may include a screw 10 configured to affix threads 102 within the device. In some further embodiments, a screw installation tool 300 may be used for affixing screw 10 with precise positioning.

In certain embodiments, drive assembly 11A may comprise a shaft 24 and a gear assembly 25. Shaft 24 is configured to engage with tension adjustment tool 200, whereby the tension adjustment tool 200 may be used to rotate the shaft. The gear assembly 25 is configured to transfer rotational motion of tool 200/shaft 24 to bobbin 11 to effectuate its axial rotation for winding or unwinding threads 102. In certain embodiments, the gear assembly 25, shaft 24, and bobbin 11 all rotate about rotational axes which may be parallel or co-axial one another (i.e., a central cylindrical axis or an off-center but parallel an axis of symmetry in the case of cycloidal motion.

In one embodiment, bobbin 11 includes an upper bobbin section 12 and a lower bobbin section 18. In some embodiments, a mid-bobbin section 16 is provided between upper and lower bobbin sections, but not necessarily so. In further embodiments, shaft 24 may comprise a cylindrical/symmetrical bottom portion 24A with an eccentric (i.e., off center) shaft neck 24C. The gear assembly 25 may comprise an eccentricity compensator 20 below lower bobbin section 18, an internal gear 22 (also referred to as a "cycloidal motion gear 22" or "cycloidal gear 22") below compensator 20, and a gear ring 26D. In some embodiments, shaft 24 (also referred to as "eccentric shaft 24") arranged below cycloidal gear 22, and is mechanically coupled thereto for driving its cycloidal motion. In one embodiment, shaft neck 24C may be frictionally fitted into a central opening in cycloidal gear 22. In some further embodiments, shaft neck 24C may pass through a central opening in compensator 20.

In further embodiments, device 100 may comprise a housing comprising a top cover 14 and a bottom cover 26, wherein gear ring 26D may be an integral component of bottom cover 26. In some embodiments, top cover 14 and bottom cover 26 are configured to interlock for retaining the internal assembly components, i.e., bobbin 11, eccentricity compensator 20, cycloidal gear 22, and eccentric shaft 24, while providing access to screw 10 and eccentric shaft 24. Top cover 14 and bottom cover 26 are further configured to allow threads 102 to pass through device 100, as will be described.

In certain embodiments, upper bobbin section 12 (also referred to as "upper bobbin 12") may include an outer vertical rim 13 surrounding an internal well 13A in which internal bobbin threading 12A for receiving screw 10 and oppositely disposed side openings 12B for receiving threads 102 are provided. In certain embodiments, internal well 13A may have a geometry that is conical, parabolic, and/or concave, or the like, as depicted in the figures. In some embodiments, internal bobbin threading 12A provides a through hole which extends out through lower bobbin section 18. In some embodiments, side openings 12B extend out though rim 13. In further embodiments, the underside of lower bobbin section 18 may comprise bottom tabs 18A configured to engage slots within eccentricity compensator 20 as will be described. In some embodiments, holes/gaps may be included in the bobbin discs for reduced weight, but not necessarily so.

In certain embodiments, top cover 14 and bottom cover 26 are configured to allow threads 102 to pass into and out of device 100 through side openings 12B in upper bobbin 12. In certain embodiments, a lower rim 14B in top cover 14 may include oppositely disposed side openings 14A configured to allow threads 102 to pass, and an upper rim 26B in bottom cover 26 may include oppositely disposed side openings 26A configured to allow threads 102 to pass. In some embodiments, lower rim 14B is configured to lockable engage with upper rim 26B, whereby side openings 14A are configured to align with side openings 26A to provide a clear and guided passage for threads 102 into the device housing. In one embodiment, mid and lower bobbin sections 16, 18 may each include bobbin discs, wherein the bobbin disc of mid-bobbin section 16 has a reduced diameter to allow reduction of the distance between openings 26A/14A in the housing. It is noted that the positions of openings 12B, and 14A/26A direct threads 102 in opposite direction to one another for maximizing tension force on the implanted sling which is continuous with threads 102 entering side openings 26A, 14A.

In certain embodiments, top cover 14 includes a central opening 14C defined by surrounding wall 14E for receiving upper bobbin 12, whereby a cylindrical surface of rim 13 fits within surrounding cylindrical opening 14E. In further embodiments, top cover 14 may also include an internal vertical wall 14D configured to slidably engage a peripheral vertical wall of mid bobbin 16. In some embodiments, these walls may be smooth so that the device housing and/or top cover 14 retains bobbin 11 in position while allowing it to rotate with minimized friction. Additionally, opening 14C allows screw 10 to threadedly engage within internal bobbin threading 12A for capturing threads 102 between screw head 10A and internal well 13A. In some embodiments, screw head 10A has a conical shape conforming to the shape of internal well 13A, thereby threads 102 passed through openings 12B are captured between screw head 10A and internal well 13A when screw 10 is threaded into internal bobbin threading 12A. In some embodiments, once threads 102 are initially adjusted, screw 10 may be inserted and threaded via screw installation tool 300 which positions screw 10 in precise alignment with internal bobbin threading 12A. In certain embodiments, the screw installation tool 300 may comprise a plurality (e.g., 3 or 4) of elastic lamellas 302 design to hold the screw and ensure its centering and correct orientation with respect to internal bobbin threading 12A. During the screwing process, lamellas 302 automatically release the screw head when screw 10 is correctly positioned within internal threading 12A. This screwing process provides improved comfort and speed of the operation since the risk of losing the screw during its installation is eliminated.

In certain embodiments, bottom cover 26 may comprise a central bottom opening 26C which provides a seat for supporting eccentric shaft 24 at its bottom portion 24A. In further embodiments, cycloid gear 22 may comprise gear teeth 22A configured to engage gear ring 26D in bottom cover 26. Neck 24C is configured to engage cycloid gear 22 for driving its eccentric motion and engagement against gear ring 26D. Thus, shaft 24 ensures that gear teeth 22A of cycloid gear 22 is rolled along the teeth of gear ring 26D, making a slow rotational movement relative to the eccentric axis. Bottom cover 26 retains shaft 24 while allowing for its rotation and vertical fixation via tension adjustment tool 200. In certain embodiments, eccentric shaft 24 may be rotated using tension adjustment tool 200 to apply rotational force/torque onto shaft 24, wherein the gear/shaft arrangement provides a mechanical advantage which allows for reduced human effort.

In certain embodiments, cycloid gear 22 may be coupled to bobbin 11 via compensator 20, which may comprise a first pair of opposing guide slots 20A configured to engage upper tabs 22B in cycloid gear, and a second pair of opposing guide slots 20B configured to engage bottom tabs 18A in lower bobbin section 18. In embodiments, guide slots 20A and 20B are each sized to allow upper tabs 22B and bottom tabs 18A to slide within the respective slot as cycloid gear 22 rotates. As such, compensator 20 transfers rotational movement of gear 22 and at least partially compensates its eccentricity via engagement between upper sliding tabs 22B in the cycloid gear and guide slots 20A of the compensator. Final compensation of eccentricity occurs in the pair of opposing guide slots 20B and bobbin 11 via the second pair of bottom sliding tabs 18A in the bobbin.

In certain embodiments, tension adjustment tool 200 may generally comprise an elongated tool body 36 including a tool head 38 at its distal end which supports a locking key 30 and lamellas 40. Locking key 30 is configured to quickly engage and disengage with bottom cover 24, wherein lamellas 40 transmit rotary movement of the tool 200 to shaft 24. More specifically, locking key 30 is configured to engage an inlet hole 24B in shaft 24, whereby lamellas 40 may capture and rotate shaft 24.

In certain embodiments, tension adjustment tool 200 may further comprise a handle base 32 including a lock button channel 35, wherein elongated tool body 36 is nested within handle base 32. In some embodiments, an internal spring (not shown) may be provided within handle base 32 below elongated tool body 36. Elongated tool body 36 may further include a lock button 34 in its lower portion which is slidably engaged within lock button channel 35.

In certain embodiments, lock button 34 and lock button channel 35 cooperate to allow tension adjustment tool 200 to switch between an unlock position in which locking key 30 is in planar alignment with lamellas 40 (see FIG. 2), and an lock position in which locking key 30 is rotated 90 degrees and is perpendicular alignment with lamellas 40 (see FIG. 3). In one embodiment, lock button channel 35 is L-shaped and includes a lower horizontal channel component 35A and a vertical channel component 35B extending upwards and perpendicularly from a first end 35C of the horizontal channel (also a vertex of the channel). In the lock position, button 34 occupies the horizontal channel component 35A and is in the vertical channel component 35B in the unlock position. When in the horizontal channel 35A, button may slide laterally within the channel when handle base 32 is rotated (illustrated in FIG. 3 as clockwise) causing handle base to twist with respect to tool body 36. This shifts button 34 to first end 35C and into vertical channel 35B to transition tool 200 to the lock position.

Thus, when tool 200 is inserted within the body and into inlet hole 24B of shaft 24, locking key 30 may be turned in a first direction to the locked state. Both inlet hole 24B of shaft 24 and locking key 30 include at least one asymmetry, such that locking key 30 is prevented from passing through inlet hole 24B when the inlet hole and locking key are misaligned. As such, tool 200 may be inserted into the body wherein locking key 30 passes through inlet hole 24B and is rotated relative to the inlet hole to lockably engage tool 200 in device 100 and prevent its accidental detachment. Tool 200 may then be further rotated to transmit a torque force for rotating shaft 24 via lamellas 40. To disengage tool 200, handle base 32 may be moved upwards with respect to elongated body to position button within first end 35C, then twisted in the opposite direction to shift button 34 into channel 35A. This movement may be performed quickly and utilizes the shape of the slot in the eccentric and the shape of the locking key in the tool head to protect against accidental premature detachment of the tool from the implant. When rotated, eccentric shaft 24 provides variable valve lift control, wherein the valve lift changes continuously from maximum to almost zero by rotating/pivoting the eccentric shaft.

Thus, the disclosed subject matter provides a system for treating urinary incontinence including an implant device for retention and adjustment of the sling threads. The design of the compensator together with the geometry and parameters of the cycloid gear, ensures self-locking of the entire assembly with a constant degree of thread tension without the use of additional locking mechanisms. This allows threads 200 to be tightened without loosening the treads, and/or needing to elevate then drop the sling.

The generally flat proportions of the device including integration of the outer gear ring into the housing allow for a low profile of the entire device while maintaining the ability to wind a sufficient amount of thread. The reduced number of moving parts needed to achieve a high gear ratio is a further contributing factor to the device's compactness and low thickness. In some embodiments, a ratio of the diameter to axis length may be at least about 3.5 to avoid risk of the rotation of the device within patient's body. Furthermore, the disclosed device and system allows for precise tension adjustment of the threads in the body to eliminate guesswork.

It shall be appreciated that while device 100 is designed to be surgically implanted in the human body for treating urinary incontinence, it may be adapted for other medical or non-medical applications where thread tension needs to be precisely adjusted or readjusted while providing stability of tension.

In certain embodiments, components of device 100 may be 3-D printed or pressed out. However, it shall be appreciated that the components of device 100 may be manufactured and assembled using any known techniques in the field. It shall be appreciated that the components of implant device 100 may comprise any alternative known materials in the field and be of any size and/or dimensions.

It shall be appreciated that the disclosed device and system can have multiple configurations in different embodiments. It shall be appreciated that the device and system described herein may comprise any alternative known materials in the field and be of any color, size, and/or dimensions. It shall be understood that the orientation or positional relationship indicated by terms such as "upper", "lower", "front", "rear", "left", "right", "top", "bottom", "inside", "outside" is based on the orientation or positional relationship shown in the accompanying drawings, which is only for convenience and simplification of describing the disclosed subject matter, rather than indicating or implying that the indicated device or element must have a specific orientation or are constructed and operated in a specific orientation, and therefore should not be construed as a limitation of the present invention.

As used herein, the articles "a" and "an" are intended to include one or more items, and may be used interchangeably with "one or more." Where only one item is intended, the term "one" or similar language is used. Also, as used herein, the terms "has", "have", "having", "with" or the like are intended to be open-ended terms. Further, the phrase "based on" is intended to mean "based, at least in part, on" unless explicitly stated otherwise.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An implant device for treating urinary incontinence, comprising:
   a bobbin on which threads of an implanted sling may be wound; and
   a drive assembly configured to rotate the bobbin, the drive assembly comprising a shaft and a gear assembly, the gear assembly configured to transfer a rotational motion of the shaft to the bobbin to effectuate an axial rotation of the bobbin,
   wherein the bobbin and drive assembly are retained in a device housing, configured to allow threads wound on the bobbin to pass,
   wherein the implant device is configured to allow for adjustment of a length of threads wound on the bobbin via rotation of the bobbin, wherein rotational axes of the bobbin, shaft, and gear assembly are co-axial and/or parallel one another,
wherein the drive assembly is a cycloidal drive.

2. The implant device of claim 1, wherein the gear assembly comprises an internal gear coupled to the shaft, the shaft configured to drive a cycloidal rotation of the internal gear.

3. The implant device of claim 2, wherein the shaft comprises a symmetrical bottom portion and an eccentric shaft neck.

4. The implant device of claim 3, wherein the eccentric shaft neck is directly coupled to the internal gear.

5. The implant device of claim 2, further comprising a gear ring, wherein external teeth of the internal gear are configured to cycloidally roll against internal teeth in the gear ring when the internal gear is driven by the shaft.

6. The implant device of claim 5, wherein the gear ring is an integral component of the device housing.

7. The implant device of claim 2, wherein the gear assembly further comprises an eccentricity compensator between the bobbin and the internal gear, the eccentricity compensator being coupled to an underside of the bobbin and to an upper side of the internal gear and is configured to drive a cylindrical rotation of the bobbin.

8. The implant device of claim 7, wherein the eccentricity compensator includes a first pair of opposing guide slots configured to slidable engage a corresponding pair of upper tabs in the cycloid gear, and a second pair of opposing guide slots configured to slidably engage a corresponding pair of bottom tabs in the underside of the bobbin, wherein as the internal gear cycloidally rotates, the upper tabs slide within the first pair of guide slots and the bottom tabs slide within the second pair of guide slots.

9. The implant device of claim 1, wherein the drive assembly may be actuated via a tool configured to detachably engage the shaft for driving a rotation of the shaft.

10. The implant device of claim 9, wherein the shaft includes a bottom portion which provides an inlet hole for receiving said tool, the device housing including a bottom opening that provides access to said inlet hole in the shaft.

11. The implant device of claim 1, wherein the device housing comprises a top cover and a bottom cover configured to interlock with the top cover.

12. The implant device of claim 1 wherein the device housing includes opposing holes through which threads wound on the bobbin may pass.

13. The implant device of claim 1, wherein an upper section of the bobbin comprises a central threaded hole configured to receive a screw for affixing threads wound on the bobbin.

14. The implant device of claim 2, wherein the upper section of the bobbin includes openings through which ends of threads wound on the bobbin may pass, wherein the upper section of the bobbin is further shaped to enable said screw to capture the ends of said threads when said threads are wound on the bobbin and when the screw is threaded through said central threaded hole, wherein the ends of the threads are captures between a head of the screw and a wall surrounding the central threaded hole.

15. The implant device of claim 14, wherein the wall surrounding the central threaded hole is a well which is shaped to match a shape of the screw head.

16. The implant device of claim 15, wherein the well has a conical, parabolic, and/or concaved profile.

17. The implant device of claim 13, wherein a top section of the housing includes an opening configured to allow said screw to pass into the threaded hole in the upper section of the bobbin.

18. The implant device of claim 1, wherein the device is disc shaped with a diameter to axial length ratio of at least about 3.5.

* * * * *